(12) United States Patent
Sinderby et al.

(10) Patent No.: US 7,909,034 B2
(45) Date of Patent: Mar. 22, 2011

(54) COMBINED POSITIVE AND NEGATIVE PRESSURE ASSIST VENTILATION

(75) Inventors: Christer Sinderby, Toronto (CA); Jennifer Beck, Toronto (CA); Christer Ström, Pitea (SE)

(73) Assignee: Maquet Critical Care AB, Solna (SE)

( * ) Notice: Subject to any disclaimer, the term of this patent is extended or adjusted under 35 U.S.C. 154(b) by 913 days.

(21) Appl. No.: 10/576,636

(22) PCT Filed: Oct. 21, 2004

(86) PCT No.: PCT/CA2004/001851
§ 371 (c)(1),
(2), (4) Date: Mar. 12, 2007

(87) PCT Pub. No.: WO2005/039679
PCT Pub. Date: May 6, 2005

(65) Prior Publication Data
US 2008/0115786 A1 May 22, 2008

Related U.S. Application Data

(60) Provisional application No. 60/514,449, filed on Oct. 23, 2003.

(51) Int. Cl.
*A61M 16/00* (2006.01)
(52) U.S. Cl. ......... 128/204.23; 128/204.18; 128/204.21; 128/204.26; 128/205.12; 128/205.13; 128/205.14; 600/529; 600/546; 601/41; 601/43; 601/44; 601/9; 601/11
(58) Field of Classification Search .............. 601/41, 601/43, 44, 6, 9, 10, 11; 128/204.18, 204.21, 128/204.23, 204.26, 205.12, 205.13, 205.14; 600/529, 546
See application file for complete search history.

(56) References Cited

U.S. PATENT DOCUMENTS
2,648,331 A * 8/1953 Bennett ................... 601/43
(Continued)

FOREIGN PATENT DOCUMENTS
WO WO 99/43374 9/1999
(Continued)

OTHER PUBLICATIONS

Supplementary European Search Report, issued in European Application No. 04789758.2, dated Mar. 18, 2009.

*Primary Examiner* — Justine R Yu
*Assistant Examiner* — Clinton Ostrup
(74) *Attorney, Agent, or Firm* — Fulbright & Jaworski LLP (57) ABSTRACT

The present invention relates to a method of delivering combined positive and negative pressure assist ventilation to a patient, wherein a positive pressure is applied to the patient's airways to inflate the patient's lungs, a negative pressure is applied around the patient's ribcage and/or abdomen in order to reduce a load imposed by the ribcage and/or abdomen on the patient's lungs, and application of the positive and negative pressures is synchronized. The present invention also relates to a system for delivering combined positive and negative pressure assist ventilation to a patient, comprising a positive pressure ventilator connected to the patient's airways for applying a positive pressure to the patient's airways to inflate the patient's lungs, a negative pressure ventilator installed on the patient's ribcage and/or abdomen for applying a negative pressure around the patient's ribcage and/or abdomen in order to reduce a load imposed by the ribcage and/or abdomen on the patient's lungs, and a controller for synchronizing operation of the positive and negative pressure ventilators.

47 Claims, 6 Drawing Sheets

U.S. PATENT DOCUMENTS

| | | | | |
|---|---|---|---|---|
| 2,822,803 A | 2/1958 | Huxley, III et al. | ............ | 601/43 |
| 3,037,498 A | 6/1962 | Smith | ............ | 601/43 |
| 3,333,581 A | 8/1967 | Robinson et al. | ............ | 601/44 |
| 4,257,407 A | 3/1981 | Macchi | ............ | 601/44 |
| 4,481,938 A | 11/1984 | Lindley | ............ | 601/43 |
| 4,930,498 A | 6/1990 | Hayek | ............ | 601/44 |
| 4,982,735 A | 1/1991 | Yagata et al. | ............ | 128/204.23 |
| 5,299,599 A | 4/1994 | Farmer et al. | ............ | 197/625.22 |
| 5,513,631 A * | 5/1996 | McWilliams | ............ | 128/204.23 |
| 5,749,830 A | 5/1998 | Kaneko et al. | ............ | 600/160 |
| 5,806,512 A * | 9/1998 | Abramov et al. | ............ | 128/204.18 |
| 5,820,560 A | 10/1998 | Sinderby et al. | ............ | 600/546 |
| 5,871,008 A | 2/1999 | Poon et al. | ............ | 128/202.12 |
| 6,273,088 B1 | 8/2001 | Hillsman | ............ | 128/204.23 |
| 6,461,315 B1 * | 10/2002 | Gattinoni | ............ | 601/41 |
| 6,779,523 B2 | 8/2004 | Luppi | ............ | 128/205.26 |

FOREIGN PATENT DOCUMENTS

WO     WO 01/08735     2/2001

* cited by examiner

FIG_8

COMBINED POSITIVE AND NEGATIVE PRESSURE ASSIST VENTILATION

This application is a national phase application under 35 U.S.C. §371 of International Application No. PCT/CA2004/001851 filed 21 Oct. 2004, which claims priority to U.S. Provisional Application No. 60/514,449 filed 23 Oct. 2003, the contents of which are incorporated herein by reference in their entirety.

FIELD OF THE INVENTION

The present invention relates to combined positive and negative pressure assist ventilation of a patient.

BACKGROUND OF THE INVENTION

Mechanical assist ventilation is delivered to a patient in order to maintain adequate alveolar ventilation by partially or totally substituting the function of the presumably weak or failing respiratory muscle(s). Initially, it was found preferable to deliver mechanical assist ventilation to a patient by applying a negative pressure around the patient's ribcage and/or abdomen; the so-called negative pressure assist ventilation. In fact, negative pressure assist ventilation creates a partial vacuum around the patient's ribcage and/or abdomen to induce inspiration. This mode of mechanical assist ventilation proved useful, but restricted physical access to the patient during ventilation.

Nowadays, mechanical assist ventilation is delivered, with a few exceptions, by applying a positive pressure to the patient's airways; the so-called positive pressure assist ventilation. In order to completely unload the patient's inspiratory muscles with positive pressure assist ventilation, it is necessary to apply a positive pressure that is capable not only to inflate the lungs, but also to displace the chest wall and the abdomen. In practice, this requires application of a positive pressure exceeding the transpulmonary pressure; the transpulmonary pressure is the pressure required to inflate the patient's lungs alone. A high inspiratory positive assist pressure increases the risk for barotrauma and pneumothorax, and can have a negative effect on hemodynamics.

Also, excessive inspiratory loads imposed by the patient's abdomen and/or ribcage may occur with obesity, reduced compliance due to abdominal distension, dynamic hyperinflation, and/or deformities of the chest wall. Obviously, higher inspiratory positive assist pressure supplied to the patient's airways is required to overcome these additional inspiratory loads.

Finally, the current commercially available modes of both positive and negative pressure assist ventilation presents the following limitation: the pneumatic system, designed to respond to the patient's effort, induces a time lag that can influence the patient's breathing pattern, leading to deterioration of the patient-ventilator synchrony. This situation is often referred to as the patient "fighting the ventilator". In order to avoid the patient "fighting the ventilator", increased patient sedation and even respiratory muscle paralysis is often required.

SUMMARY OF THE INVENTION

In accordance with the present invention, there is provided a method of delivering combined positive and negative pressure assist ventilation to a patient, comprising applying a positive pressure to the patient's airways to inflate the patient's lungs, applying a negative pressure around the patient's ribcage and/or abdomen in order to reduce a load imposed by the ribcage and/or abdomen on the patient's lungs, and synchronizing application of the positive and negative pressures.

The present invention also relates to a system for delivering combined positive and negative pressure assist ventilation to a patient, comprising first means for applying a positive pressure to the patient's airways to inflate the patient's lungs, second means for applying a negative pressure around the patient's ribcage and/or abdomen in order to reduce a load imposed by the ribcage and/or abdomen on the patient's lungs, and means for synchronizing operation of the first and second pressure-applying means.

The present invention is further concerned with a system for delivering combined positive and negative pressure assist ventilation to a patient, comprising a positive pressure ventilator connected to the patient's airways for applying a positive pressure to the patient's airways to inflate the patient's lungs, a negative pressure ventilator installed on the patient's ribcage and/or abdomen for applying a negative pressure around the patient's ribcage and/or abdomen in order to reduce a load imposed by the ribcage and/or abdomen on the patient's lungs, and a controller for synchronising operation of the positive and negative pressure ventilators.

The foregoing and other objects, advantages and features of the present invention will become more apparent upon reading of the following non restrictive description of illustrative embodiments thereof, given by way of example only with reference to the accompanying drawings.

BRIEF DESCRIPTION OF THE ILLUSTRATIVE EMBODIMENT

In accordance with the non-restrictive illustrative embodiment of the method according to the present invention, a positive pressure is applied to the patient's lungs in order to inflate the lungs and a negative pressure is applied around the patient's ribcage and/or abdomen to reduce the load imposed by the ribcage and/or abdomen on the lungs.

Figure 1:
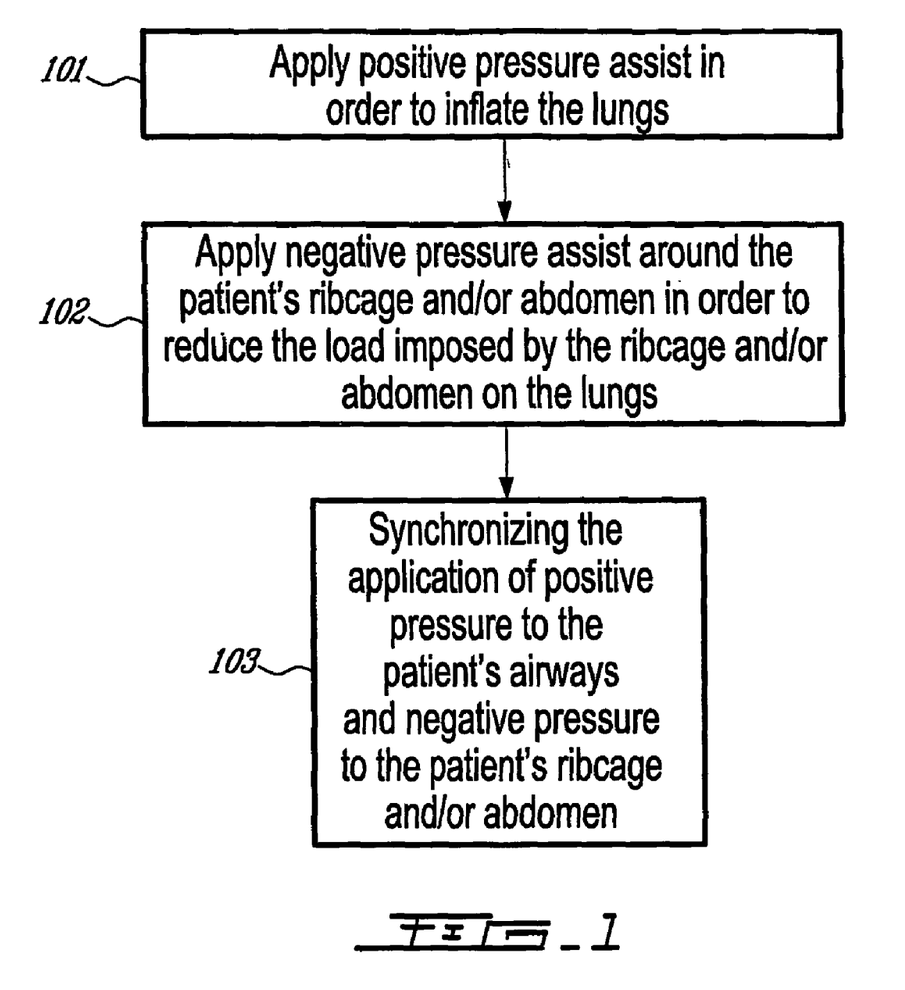
FIG. 1 is a flow chart of a non-restrictive illustrative embodiment of the method according to the present invention, for applying both a positive pressure to the patient's airways in order to inflate the lungs and a negative pressure around the patient's ribcage and/or abdomen in order to reduce the load imposed by the ribcage and/or abdomen on the lungs.

The method according to the non-restrictive illustrative embodiment of the present invention comprises, as illustrated in FIG. 1, the following operations:

Operation 101

Positive pressure is applied to the patient's airways to deliver assist ventilation, i.e. to substitute respiratory muscles' work to inflate the lungs.

Operation 102

Along with operation 101, negative pressure is applied around the patient's ribcage and/or abdomen to reduce the load imposed by the ribcage and/or abdomen on the lungs. More specifically, the negative pressure assist substitutes for respiratory muscles' work to displace the patient's ribcage and/or abdomen.

Operation 103

This operation consists of synchronizing application of positive pressure to the patient's airways and negative pressure to the patient's ribcage and/or abdomen.

Figure 2:
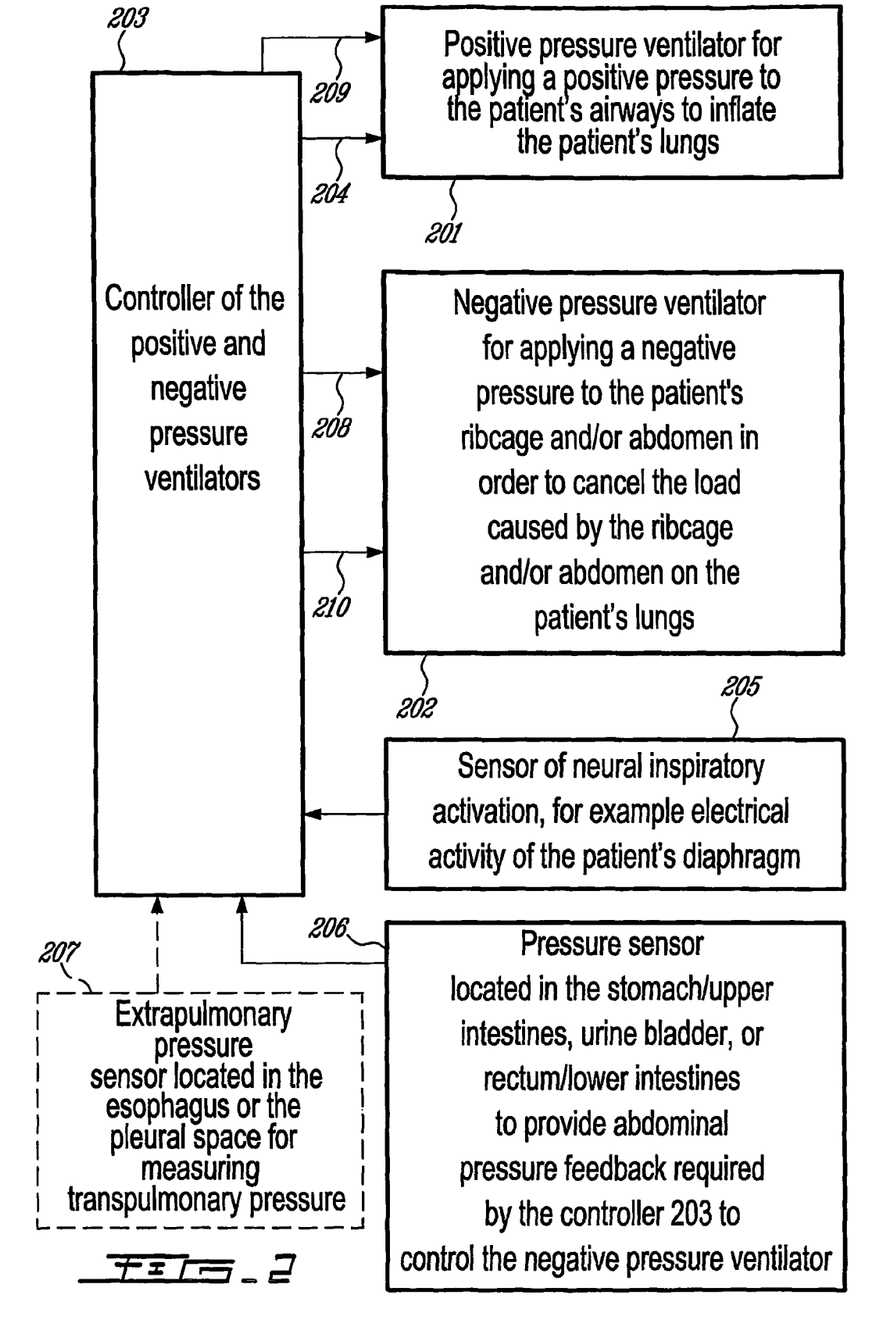
FIG. 2 is a block diagram of a non-restrictive illustrative embodiment of the system according to the present invention, for applying both a positive pressure to the patient's airways in order to inflate the lungs and a negative pressure around the patient's ribcage and/or abdomen in order to reduce the load imposed by the ribcage and/or abdomen on the lungs.
Figure 3:
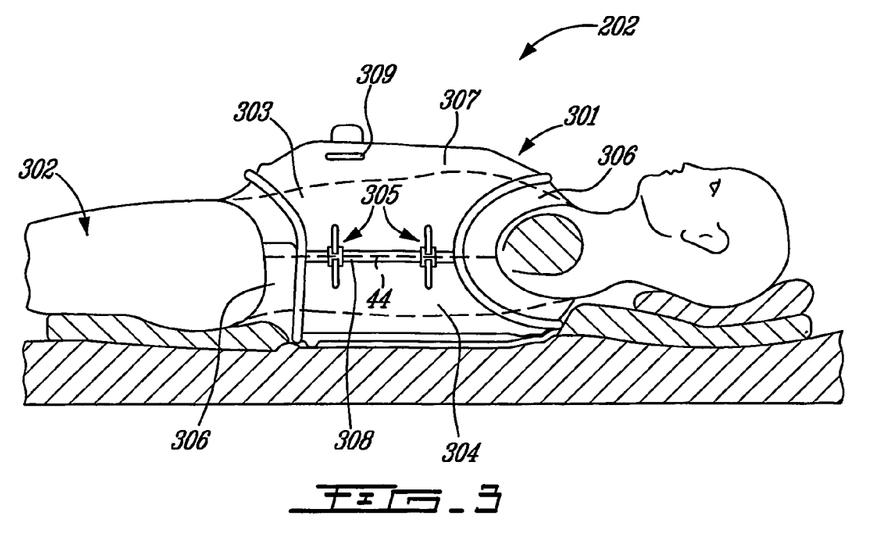
FIG. 3 is a side elevational view of an example of negative pressure ventilator.

The operations 101-103 of FIG. 1 can be performed through the system of FIGS. 2 and 3.

The system of FIG. 2, for delivering combined positive and negative pressure assist ventilation to a patient first comprises a positive pressure ventilator 201 for applying positive pressure assist ventilation (flow and/or volume) required to overcome the elastic and resistive loads related to inflation of the patient's lungs. More specifically, the positive pressure ventilator 201 will apply a positive pressure to the patient's airways to inflate the patient's lungs. Non-restrictive examples of positive pressure assist ventilation are described in U.S. Pat. No. 5,820,560 granted to Sinderby et al on Oct. 13, 1998 and U.S. Pat. No. 6,588,423 (Sinderby) issued on Jul. 8, 2003. The subject matter of these two US patents is herein incorporated by reference.

The system of FIG. 2 further comprises a negative pressure ventilator 202 structured for applying a negative pressure (flow and/or volume) around the patient's ribcage and/or abdomen to cancel and/or reduce the load caused by the ribcage and/or abdomen on the patient's lungs.

Referring to FIG. 3, an example of negative pressure ventilator 202 is illustrated. The negative pressure ventilator 202 comprises a ventilator shell 301, a patient 302 requiring negative pressure ventilatory assist wearing this ventilator shell 301. Of course, any other device for delivering negative pressure could of course be used in combination with the neural controller 203 of FIG. 2, e.g. a cuirass, an iron lung, a poncho, etc. Also, the device for delivering negative pressure does not need to be leak proof since the neural controller such as 203 will compensate for such leak.

The ventilator shell 301 extends over the ribcage and abdomen area of the patient 302 and consists of two half-shell sections 303 and 304 that are not identical but respectively shaped to serve as ventral and dorsal half-shell sections. As illustrated in FIG. 3, the half-shell sections 303 and 304 co-operate to enclose the major portion of the ribcage and abdomen of the patient 302.

The shell sections 303 and 304 are firmly secured together on opposite sides of the patient's body by respective pairs of clamps 305.

At the two ends of the ventilator shell 301, sealing lips 306 are intended to press against the skin of the patient 302 and thereby bound an airtight chamber 307 within the shell 301 for application of a negative pressure to the patient's ribcage and abdomen. Seals such as 308 are provided for sealing the joints between the two half-shell sections 303 and 304 on the opposite sides of the patient's body, thereby making these joints airtight.

The ventilator 202 produces a negative pressure or vacuum in the chamber 307 to cancel and/or reduce the load of the patient's ribcage and abdomen on the lungs. The negative pressure or vacuum is applied to the chamber 307 through a port 309 in the ventral half-shell section 303.

Negative pressure ventilators are believed to be otherwise well known to those of ordinary skill in the art and accordingly will not be further described in the present specification.

The system of FIG. 2 further comprises a controller 203 used to control the positive and negative pressure ventilators 201 and 202.

Still referring to FIG. 2, the controller 203 synchronizes triggering and termination of the application, during inspiration, of positive pressure to the patient's airways and negative pressure around the patient's ribcage and/or abdomen. For that purpose, the controller 203 derives triggering and termination signals 204 and 208 applied to the ventilators 201 and 202, respectively. The signals 204 and 208 can be derived from neural inspiratory activation, for example electrical activity of the patient's diaphragm or other respiratory-related muscle, detected through a sensor 205. A non-restrictive example of neural triggering and termination of assist ventilation is described in the above mentioned U.S. Pat. No. 6,588,423 granted Sinderby on Jul. 8, 2003.

The level of positive pressure applied to the patient's lungs during inspiration can be manually set by the medical personnel or adjusted as a function of the neural inspiratory activation, for example the electrical activity of the patient's diaphragm or other respiration-related muscle. In the latter case, the controller 203 produces a positive pressure level control signal 209 for example in response to the electrical activity of the patient's diaphragm or other respiratory-related muscle as detected by the sensor 205. The signal 209 controls the ventilator 201 to adjust the level of assist ventilation positive pressure 0 to the required level. For example, the level of positive pressure applied to the patient's lungs will be adjusted in proportion to the level of electrical activity of the patient's diaphragm or other respiratory-related muscle. An example of positive pressure assist level adjustment is described in the above mentioned U.S. Pat. No. 5,820,560 granted to Sinderby et al on Oct. 13, 1998.

The level of negative pressure applied around the patient's ribcage and/or abdomen can be adjusted as a fraction of the positive pressure delivered to the patient; alternatively, 50% of the pressure target can be delivered to the patient as positive pressure and the other 50% of the pressure target can be delivered as negative pressure. A more physiological approach would be to use feedback from the abdominal pressure. The controller 203 produces, for that purpose, a negative pressure level control signal 210 applied to the negative pressure ventilator 202. The abdominal pressure feedback supplied to the controller 203 for producing the signal 210 and controlling the level of negative pressure applied around the patient's ribcage and/or abdomen could be obtained via a pressure sensor 206 located, for example, in the stomach/upper intestines, urine bladder, rectum/lower intestines, etc. This process will be described in detail in the following description.

The abdominal pressure can be measured, for example, through a small gastric balloon mounted on an esophageal catheter and inserted in the stomach/upper intestines. This small gastric balloon, inflated with gas, will be subjected to the abdominal pressure and associated with an outside gas pressure detector for detecting this abdominal pressure.

Alternatively, pressure can be measured through an extrapulmonary pressure sensor 207. This extrapulmonary pressure sensor 207 will be located, for example, in the patient's esophagus or pleural space. Again, this extrapulmonary pressure sensor 207 can comprise a small balloon mounted on an esophageal catheter and inserted in the patient's esophagus or pleural space. This small balloon, inflated with gas, will be subjected to the intrathoracic pressure and associated with an outside gas pressure detector for detecting the transpulmonary pressure. Application of negative pressure can then be quantified with respect to how much it reduces transpulmonary pressure i.e. the pressure distending lung including airways and alveoli.

Moreover, an intrathoracic pressure estimate could be obtained by measuring an airway pressure deflection during a patient's airway occlusion. In case of intrinsic PEEP, this includes an extrapolation for the period between the onset of electrical activity of the patient's diaphragm activity and the onset of the patient's airway pressure deflection.

In fact, the abdominal pressure can be measured through any other suitable means known to those of ordinary skill in the art and capable of measuring abdominal pressure from locations as various as the patient's airways, esophageus, pleural space, stomach/upper intestines, urine bladder, rectum/lower intestines, etc.

Application of Positive Pressure Assist Ventilation (101 of FIG. 1)

Figure 4:
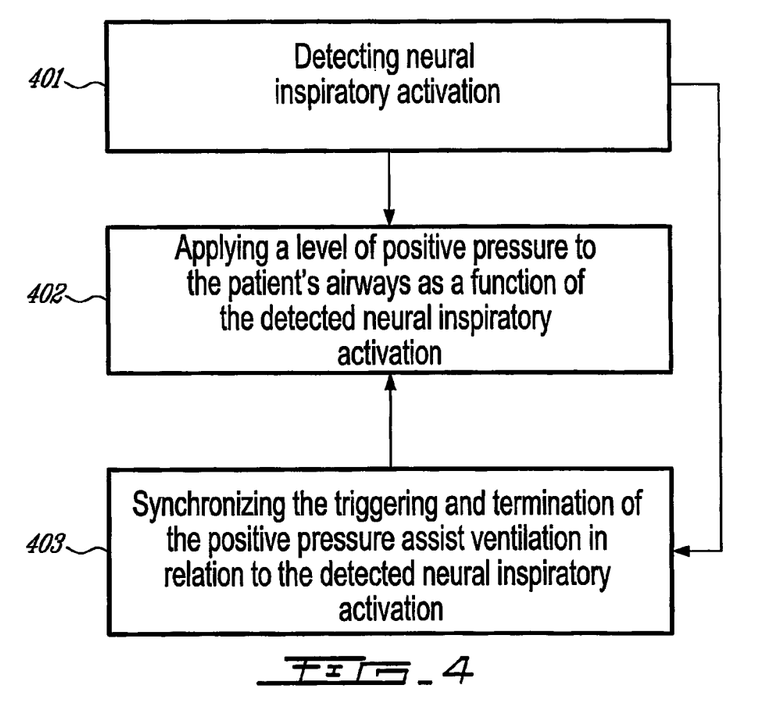
FIG. 4 is a flow chart of a first non-restrictive illustrative embodiment of process for applying the positive pressure to the patient's airways in order to inflate the lungs.

First Non-Limitative Example of Process for Controlling the Level of Positive Pressure Applied to the Patient's Airways (FIG. 4)

Operation 401

According to this first non limitative example, neural inspiratory activation is detected through the sensor 205 of FIG. 2. For example, the sensor 205 can detect electrical activity of the patient's diaphragm or other respiratory-related muscle. A non-limitative example of detection of the electrical activity of the patient's diaphragm is described in the above mentioned U.S. Pat. No. 5,820,560 granted to Sinderby et al on Oct. 13, 1998.

Operation 402

The controller 203 controls the positive pressure ventilator 201 through the level control signal 209 to apply to the patient's airways a level of positive pressure adjusted as a function of the detected neural inspiratory activation, for example the electrical activity of the patient's diaphragm or other respiratory-related muscle. For example, the level of the positive pressure applied to the patient's airways can be proportional to the detected level of neural inspiratory activation. A non-restrictive example of inspiratory proportional pressure assist ventilation is described in the above mentioned U.S. Pat. No. 5,820,560 granted to Sinderby et al on Oct. 13, 1998.

Operation 403

As described in the foregoing description, the controller 203 synchronizes the triggering and termination of the cyclically induced positive pressure assist ventilation to the patient's spontaneous breathing. For that purpose, the controller 203 derives the triggering and termination signal 204, applied to the ventilator 201, from the neural inspiratory activation for example the electrical activity of the patient's diaphragm or other respiratory-related muscle detected through the sensor 205. A non-restrictive example of neural triggering and termination of assist ventilation is described in the above mentioned U.S. Pat. No. 6,588,423 granted Sinderby on Jul. 8, 2003.

Operations 401-403 can be performed every inspiratory cycle. Alternatively, the inspiratory cycle can be divided into a plurality of segments and operations 401 and 402 can be performed every cycle segment.

Figure 5:
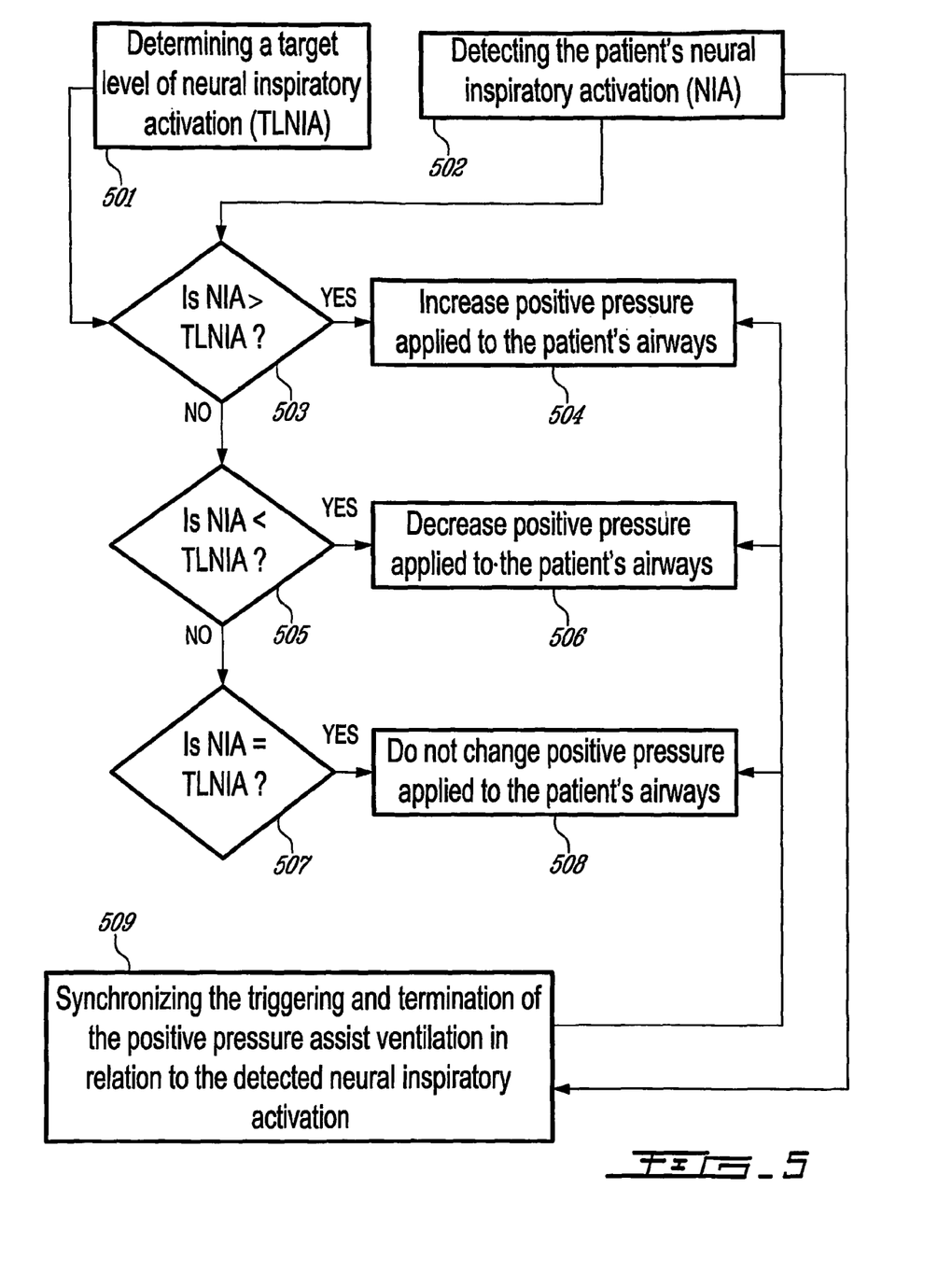
FIG. 5 is a flow chart of a second non-restrictive illustrative embodiment of process for applying the positive pressure to the patient's airways in order to inflate the lungs.

Second Non-Limitative Example of Process for Controlling the Level of Positive Pressure Applied to the Patient's Airways (FIG. 5)

Operation 501

The non-limitative process of FIG. 5 first determines a target level of the neural inspiratory activation, for example the electrical activity of the patient's diaphragm or other respiratory-related muscle. As a non-limitative example, this target level can be determined by the medical personnel for each individual patient depending on the condition of the patient.

Operation 502

The sensor 205 of FIG. 2 detects the patient's neural inspiratory activation, for example the electrical activity of the patient's diaphragm or other respiratory-related muscle.

Operation 503

If the controller 203 determines that the detected patient's neural inspiratory activation (Operation 502) is higher than the target level of neural inspiratory activation (Operation 501), operation 504 is performed.

Operation 504

The level of positive pressure applied to the patient's airways is increased, for example by a predetermined step.

Operation 505

If the controller 203 determines that the detected patient's neural inspiratory activation, for example the electrical activity of the patient's diaphragm or other respiratory-related muscle (Operation 502) is lower than the target level of neural inspiratory activation (Operation 501), Operation 506 is performed.

Operation 506

The level of positive pressure applied to the patient's airways is decreased, for example by a predetermined step.

Operation 507

If the controller 203 determines that the detected patient's neural inspiratory activation (Operation 502) is equal to the target level or within an acceptable range of the target level of the patient's neural inspiratory activation (Operation 501), Operation 508 is performed.

Operation 508

The level of positive pressure applied to the patient's airways is not changed.

Operation 509

As described in the foregoing description, the controller 203 synchronizes the triggering and termination of the cyclically induced positive pressure assist ventilation to the patient's spontaneous breathing. For that purpose, the controller 203 derives the triggering and termination signal 204, applied to the ventilator 201, from the neural inspiratory activation for example the electrical activity of the patient's diaphragm or other respiratory-related muscle detected through the sensor 205 (Operation 502). A non-restrictive example of neural triggering and termination of assist ventilation is described in the above mentioned U.S. Pat. No. 6,588,423 granted Sinderby on Jul. 8, 2003.

Operations 502-508 can be performed every inspiratory cycle. Alternatively, the inspiratory cycle can be divided into a plurality of segments and operations 502-508 can be performed every cycle segment. Finally, operations 502-508 can also be applied for time segments longer than one inspiratory cycle.

An example of target drive pressure assist ventilation is described in published Canadian patent application No. 2,379,671 (Sinderby et al) filed on Jul. 27, 2000, of which the subject matter is herein incorporated by reference.

Application of Negative Pressure Assist Ventilation (102 of FIG. 1)

Figure 6:
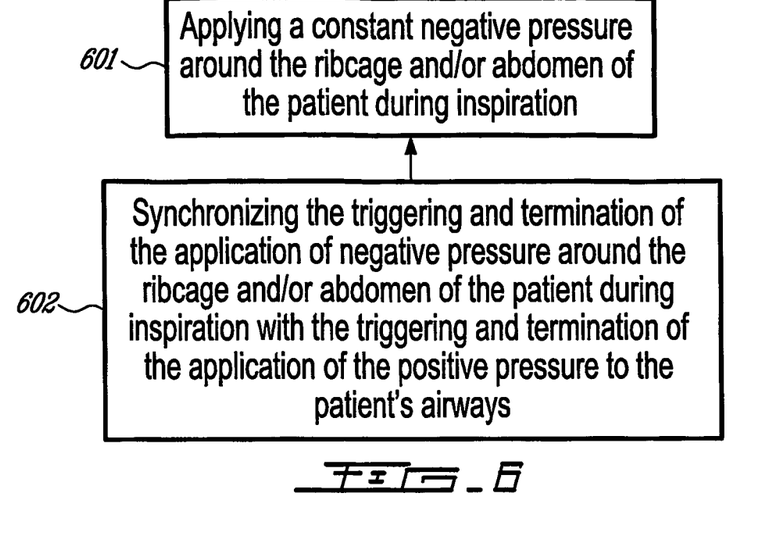
FIG. 6 is a flow chart of a first non-restrictive illustrative embodiment of process for applying a negative pressure around the patient's ribcage and/or abdomen in order to reduce the load imposed by the ribcage and/or abdomen on the lungs.

First Non-Restrictive Illustrative Process for Applying a Negative Pressure Around the Patient's Ribcage and/or Abdomen (FIG. 6)

Operation 601

The simplest method for applying negative pressure around the patient's ribcage and/or abdomen consists of applying a fixed negative pressure around the ribcage and/or abdomen of the patient during inspiration and/or expiration.

Operation 602

Triggering and termination of the application of negative pressure around the patient's ribcage and/or abdomen is synchronized with triggering and termination of the application of positive pressure to the patient's airways.

However, it is within the scope of the present invention to use any other suitable type of control for the triggering and termination of the application of negative pressure around the patient's ribcage and/or abdomen.

Operations 601 and 602 can be performed every inspiratory cycle. The negative pressure application in 601 is not restricted to inspiration only; negative pressure can also be applied during the expiratory phase, where the magnitude of the negative pressure does not have to be same as during the inspiratory phase.

Figure 7:
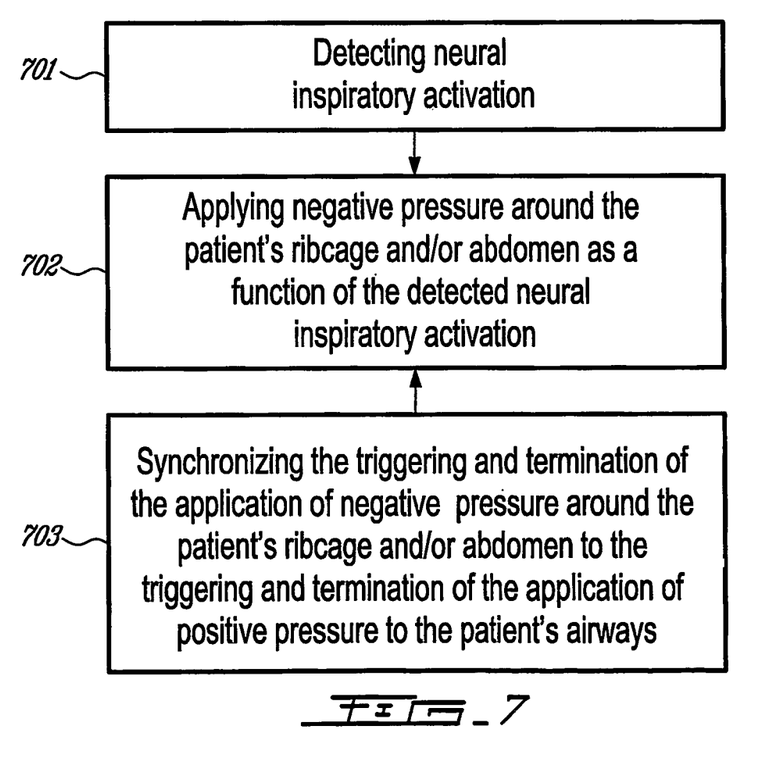
FIG. 7 is a flow chart of a second non-restrictive illustrative embodiment of process for applying a negative pressure around the patient's ribcage and/or abdomen in order to reduce the load imposed by the ribcage and/or abdomen on the lungs.

Second Non-Restrictive Illustrative Process for Applying a Negative Pressure Around the Patient's Ribcage and/or Abdomen (FIG. 7)

Operation 701

According to this second non limitative example, neural inspiratory activation is detected through the sensor 205 of FIG. 2. For example, the sensor 205 can detect electrical activity of the patient's diaphragm or other respiratory-related muscle.

Operation 702

The controller 203 controls the negative pressure ventilator 202 through the level control signal 210 to apply a level of negative pressure around the patient's ribcage and/or abdomen as a function of the detected neural inspiratory activation, for example the electrical activity of the patient's diaphragm. For example, the level of the negative pressure applied around the patient's ribcage and/or abdomen can be proportional to the detected level of neural inspiratory activation. A non-restrictive example of inspiratory proportional pressure assist ventilation is described in the above mentioned U.S. Pat. No. 5,820,560 granted to Sinderby et al on Oct. 13, 1998.

Operation 703

Triggering and termination of the application of negative pressure around the patient's ribcage and/or abdomen is synchronized with triggering and termination of the application of positive pressure to the patient's airways.

However, it is within the scope of the present invention to use any other suitable type of control for the triggering and termination of the application of negative pressure around the patient's ribcage and/or abdomen.

Operations 701-703 can be performed every inspiratory cycle. Alternatively, the inspiratory cycle can be divided into a plurality of segments and operations 701 and 702 can be performed every cycle segment.

Figure 8:
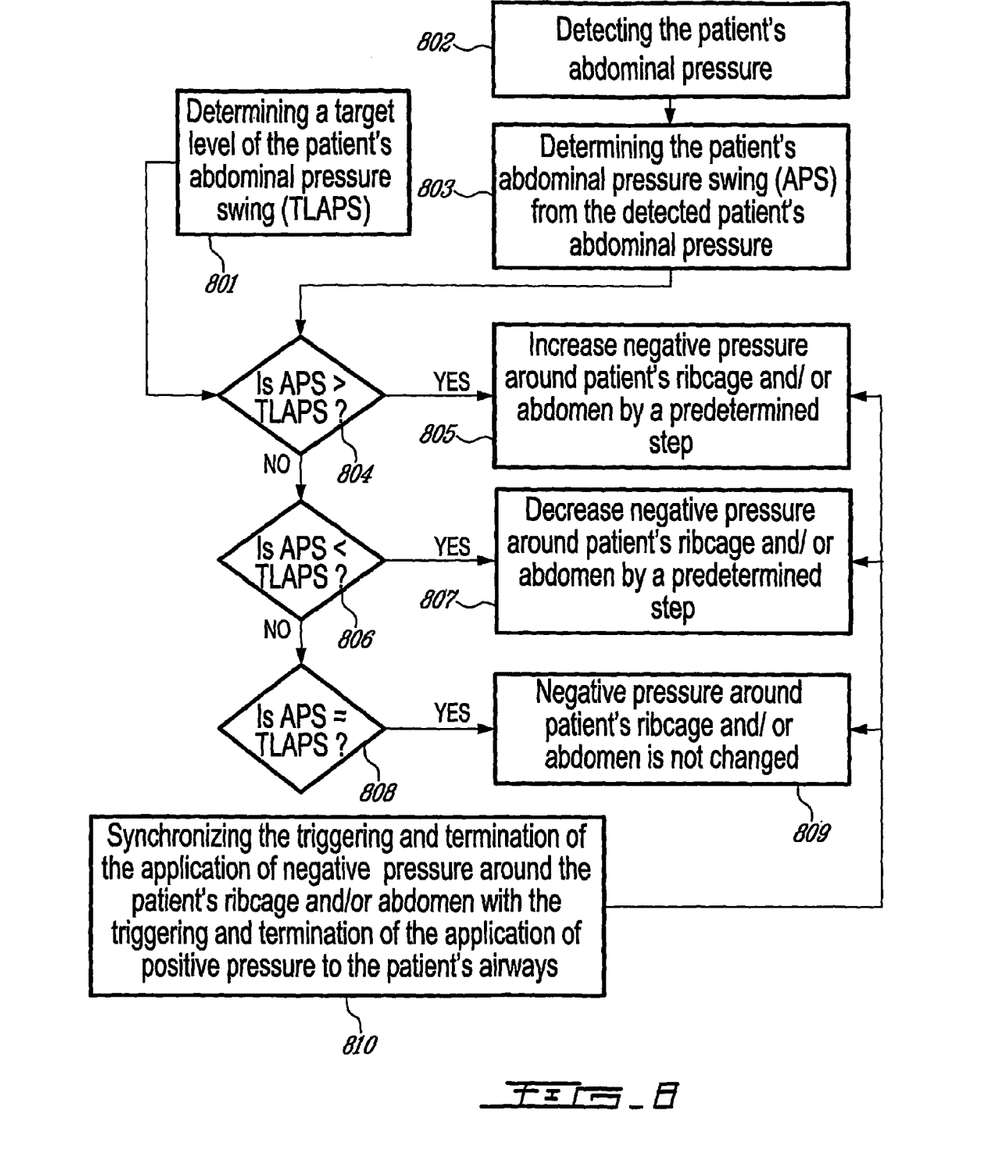
FIG. 8 is a flow chart of a third non-restrictive illustrative embodiment of process for applying a negative pressure around the patient's ribcage and/or abdomen in order to reduce the load imposed by the ribcage and/or abdomen on the lungs.

Third Non-Limitative Example of Process for Applying a Negative Pressure Around the Patient's Ribcage and/or Abdomen (FIG. 8)

Operation 801

The non-limitative process of FIG. 8 first determines a target level of abdominal pressure swing of the patient. The abdominal pressure swing is the variation of abdominal pressure during a complete cycle of inspiration. For example, the target level of abdominal pressure swing can be determined on the basis of previously measured absolute, peak, mean and/or area/integral values of abdominal pressure swings with or without a range.

In this particular case, the objective is to control the negative pressure assist ventilation so as to reduce the abdominal pressure swing during inspiration. According to this non-restrictive illustrative embodiment, this is achieved by setting a target level of abdominal pressure swing.

Operation 802

The pressure sensor 206 of FIG. 2 detect the patient's abdominal pressure during inspiration, using any method known to those of ordinary skill in the art, including those as described in the foregoing description.

Operation 803

The patient's abdominal pressure swing is determined by the controller 203 from the patient's abdominal pressure detected during inspiration through the pressure sensor 206 of FIG. 2 (Operation 801).

Operation 804

If the controller 203 determines that the detected patient's abdominal pressure swing (Operation 803) is higher than the target level of abdominal pressure swing (Operation 801), Operation 805 is conducted.

Operation 805

The level of negative pressure applied around the ribcage and/or abdomen is increased, for example by a predetermined step.

Operation 806

If the controller 203 determines that the detected patient's abdominal pressure swing (Operation 803) is lower than the target level of abdominal pressure swing (Operation 801), Operation 807 is performed.

Operation 807

The level of negative pressure applied around the ribcage and/or abdomen is decreased, for example by a predetermined step.

Operation 808

If the controller 203 determines that the detected patient's abdominal pressure swing (Operation 803) is equal to the target level of abdominal pressure swing (Operation 801), Operation 809 is performed.

Operation 809

The level of negative pressure applied around the ribcage and/or abdomen is not changed.

Operation 810

Triggering and termination of the application of negative pressure around the patient's ribcage and/or abdomen is synchronized with triggering and termination of the application of positive pressure to the patient's airways.

However, it is within the scope of the present invention to use any other suitable type of control for the triggering and termination of the application of negative pressure around the patient's ribcage and/or abdomen.

Operations 802-810 can be performed every inspiratory cycle. Alternatively, the inspiratory cycle can be divided into a plurality of segments and operations 802-809 can be performed every cycle segment. Also, operations 802-810 can be performed during time periods longer than one inspiratory cycle.

An example of target drive pressure assist ventilation is described in the above mentioned published Canadian patent application No. 2,379,671 (Sinderby et al) filed on Jul. 27, 2000.

It should be mentioned here that a constant Negative End-Expiratory Pressure (NEEP) can be applied over the abdomen to adjust the end-expiratory lung-volume. NEEP can be applied in combination with inspiratory negative pressure assist ventilation or alone. NEEP can also be delivered in proportional response to tonic inspiratory muscle, for example the diaphragm, activation occurring during expiration.

The above-described, non-restrictive illustrative embodiments of the present invention present, amongst others, the following original features:
1. Combined use of positive and negative pressure assist ventilations;
2. Neurally controlled positive and negative pressure assist ventilations;
3. Neurally triggered and terminated positive and negative pressure assist ventilations;
4. Use of proportionality with positive and negative pressure assist ventilations;
5. Use of target drive during positive and negative pressure assist ventilations; and
6. Specific control of negative pressure assist ventilation via abdominal pressure feedback.

Also, the application of both positive and negative pressure assist ventilations presents, amongst others, the following advantages:

It makes it possible to simultaneously:
    minimize or optimize inspiratory abdominal pressure swing by applying a negative pressure around the ribcage and/or the abdomen, thus reducing the abdominal load during inspiration, and
    deliver the required volume of air to the lung by applying an additional positive pressure to the patient's airways.

A device for carrying out combined positive and negative pressure assist ventilation will not obstruct patient access as negative pressure ventilation alone would, since the positive pressure ventilation could assume 100% of the assist while the negative pressure device is removed during patient access.

The negative pressure applied around the patient's ribcage and/or abdomen eliminates both the load caused by the ribcage and/or abdomen on the patient's lungs and, thereby, the need for excessive positive pressure applied to the patient's airways.

Cyclic and/or proportional application of negative pressure around the abdomen facilitates diaphragm movement and hence, reduces the risk for airway collapse in the dependent regions of the lungs.

The positive and negative pressures can be adjusted to avoid application of excessive positive pressure to the patient's airways, and therefore to minimize hemodynamic adverse effects. Monitoring of hemodynamics will help to optimize the level of the negative pressure assist as well as the relative contribution of the positive and negative pressure assists in order to minimize these hemodynamic adverse effects.

Although the present invention has been described in the foregoing description by means of illustrative embodiments thereof, it should be kept in mind that these embodiments can be modified at will within the scope of the appended claims without departing from the spirit and nature of the subject invention.

What is claimed is:

1. A method of delivering combined positive and negative pressure assist ventilation to a patient, comprising:
    detecting neural inspiratory activation of the patient;
    applying a positive pressure to the patient's airways to inflate the patient's lungs;
    applying a negative pressure around the patient's ribcage and/or abdomen in order to reduce a load imposed by the ribcage and/or abdomen on the patient's lungs; and
    controlling application of the positive and negative pressures in response to the detected neural inspiratory activation of the patient;
    wherein controlling application of the positive and negative pressures comprises controlling a level of the positive pressure applied to the patient's airways as a function of the detected neural inspiratory activation of the patient.

2. A method of delivering combined positive and negative pressure assist ventilation as defined in claim 1, wherein controlling application of the positive and negative pressures comprises synchronizing application of the positive and negative pressures.

3. A method of delivering combined positive and negative pressure assist ventilation as defined in claim 2, wherein synchronizing application of the positive and negative pressures comprises:
    synchronizing triggering and termination of the application of the positive pressure to the patient's airways as a function of the detected neural inspiratory activation.

4. A method of delivering combined positive and negative pressure assist ventilation as defined in claim 2, wherein synchronizing application of the positive and negative pressures comprises:
    synchronizing triggering and termination of the application of negative pressure with triggering and termination of the application of positive pressure.

5. A method of delivering combined positive and negative pressure assist ventilation as defined in claim 1, comprising:
    adjusting levels of the positive and negative pressures to avoid application of excessive positive pressure to the patient's airways and thereby minimize hemodynamic adverse effects.

6. A method of delivering combined positive and negative pressure assist ventilation as defined in claim 1, wherein detecting neural inspiratory activation of the patient comprises detecting a level of neural inspiratory activation of the patient, and wherein controlling application of the positive and negative pressures comprises:
    determining a target level of neural inspiratory activation of the patient;
    comparing the detected level of neural inspiratory activation with the determined target level; and
    controlling a level of positive pressure applied to the patient's airways as a function of the comparison.

7. A method of delivering combined positive and negative pressure assist ventilation as defined in claim 6, wherein controlling application of the positive and negative pressures comprises:

synchronizing triggering and termination of the application of the positive pressure to the patient's airways in relation to the detected level of neural inspiratory activation.

8. A method of delivering combined positive and negative pressure assist ventilation as defined in claim 6, wherein controlling the level of positive pressure applied to the patient's airways comprises:
increasing the level of positive pressure applied to the patient's airways when the comparison indicates that the detected level of neural inspiratory activation of the patient is higher than the determined target level.

9. A method of delivering combined positive and negative pressure assist ventilation as defined in claim 6, wherein controlling the level of positive pressure applied to the patient's airways comprises:
decreasing the level of positive pressure applied to the patient's airways when the comparison indicates that the detected level of neural inspiratory activation of the patient is lower than the determined target level.

10. A method of delivering combined positive and negative pressure assist ventilation as defined in claim 6, wherein controlling the level of positive pressure applied to the patient's airways comprises:
maintaining a present level of positive pressure applied to the patient's airways when the comparison indicates that the detected level of neural inspiratory activation of the patient is equal to the determined target level.

11. A method of delivering combined positive and negative pressure assist ventilation as defined in claim 1, wherein applying a negative pressure around the patient's ribcage and/or abdomen comprises:
applying a constant negative pressure around the patient's ribcage and/or abdomen during patient's inspiration.

12. A method of delivering combined positive and negative pressure assist ventilation as defined in claim 1, wherein controlling application of the positive and negative pressures comprises:
controlling a level of the negative pressure applied around the patient's ribcage and/or abdomen as a function of the detected neural inspiratory activation.

13. A method of delivering combined positive and negative pressure assist ventilation as defined in claim 1, wherein applying a negative pressure around the patient's ribcage and/or abdomen comprises:
determining a target level of an abdominal pressure swing of the patient;
detecting a level of abdominal pressure swing of the patient;
comparing the detected level of abdominal pressure swing with the determined target level; and
controlling a level of negative pressure applied around the patient's ribcage and/or abdomen as a function of the comparison.

14. A method of delivering combined positive and negative pressure assist ventilation as defined in claim 13, wherein controlling the level of negative pressure applied around the patient's ribcage and/or abdomen comprises:
increasing the level of negative pressure applied around the patient's ribcage and/or abdomen when the comparison indicates that the detected level of abdominal pressure swing of the patient is higher than the determined target level.

15. A method of delivering combined positive and negative pressure assist ventilation as defined in claim 13, wherein controlling the level of negative pressure applied around the patient's ribcage and/or abdomen comprises:
decreasing the level of negative pressure applied around the patient's ribcage and/or abdomen when the comparison indicates that the detected level of abdominal pressure swing of the patient is lower than the determined target level.

16. A method of delivering combined positive and negative pressure assist ventilation as defined in claim 13, wherein controlling the level of negative pressure applied around the patient's ribcage and/or abdomen comprises:
maintaining a present level of negative pressure applied around the patient's rib age ribcage and/or abdomen when the comparison indicates that the detected level of abdominal pressure swing of the patient is equal to the determined target level.

17. A method of delivering combined positive and negative pressure assist ventilation as defined in claim 1, further comprising applying a constant Negative End-Expiratory Pressure over the abdomen to adjust an end-expiratory lung-volume.

18. A method of delivering combined positive and negative pressure assist ventilation as defined in claim 17, comprising applying the constant Negative End-Expiratory Pressure over the abdomen in combination with inspiratory negative pressure assist ventilation.

19. A method of delivering combined positive and negative pressure assist ventilation as defined in claim 17, comprising applying the constant Negative End-Expiratory Pressure over the abdomen in proportional response to tonic inspiratory muscle activation occurring during expiration.

20. A method of delivering combined positive and negative pressure assist ventilation as defined in claim 1, wherein applying a negative pressure comprises obtaining an intrathoracic pressure estimate by measuring an airway pressure deflection during a patient's airway occlusion.

21. A method of delivering combined positive and negative pressure assist ventilation as defined in claim 20, wherein, in case of intrinsic PEEP, obtaining an intrathoracic pressure estimate includes an extrapolation for the period between an onset of electrical activity of the patient's diaphragm activity and an onset of the patient's airway pressure deflection.

22. A method of delivering combined positive and negative pressure assist ventilation as defined in claim 1, wherein the negative pressure is further controlled in response to a measured abdominal pressure of the patient.

23. A system for delivering combined positive and negative pressure assist ventilation to a patient, comprising:
a sensor of neural inspiratory activation of the patient;
a positive pressure ventilator connected to the patient's airways for applying a positive pressure to the patient's airways to inflate the patient's lungs;
a negative pressure ventilator installed on the patient's ribcage and/or abdomen for applying a negative pressure around the patient's ribcage and/or abdomen in order to reduce a load imposed by the ribcage and/or abdomen on the patient's lungs; and
a controller connected to the sensor of neural inspiratory activation and to the positive and negative pressure ventilators for controlling application of the positive and negative pressures in response to the neural inspiratory activation detected by the sensor;
wherein the controller is responsive to the neural inspiratory activation detected by the sensor to control a level of positive pressure applied by the positive pressure ventilator.

24. A system for delivering combined positive and negative pressure assist ventilation as defined in claim 23, wherein the controller synchronizes operation of the positive and negative pressure ventilators to synchronize application of the positive pressure to the patient's airways and the negative pressure around the patient's ribcage and/or abdomen.

25. A system for delivering combined positive and negative pressure assist ventilation as defined in claim 23, comprising:
means for determining a target level of neural inspiratory activation of the patient;
wherein the sensor detects a level of neural inspiratory activation of the patient; and
wherein the controller comprises a comparator of the detected level of neural inspiratory activation with the determined target level to control the positive pressure ventilator in relation to this comparison.

26. A system for delivering combined positive and negative pressure assist ventilation as defined in claim 25, wherein the controller increases a level of positive pressure applied to the patient's airways when the comparison indicates that the detected level of neural inspiratory activation of the patient is higher than the determined target level.

27. A system for delivering combined positive and negative pressure assist ventilation as defined in claim 25, wherein the controller decreases a level of positive pressure applied to the patient's airways when the comparison indicates that the detected level of neural inspiratory activation of the patient is lower than the determined target level.

28. A system for delivering combined positive and negative pressure assist ventilation as defined in claim 25, wherein the controller maintains a present level of positive pressure applied to the patient's airways when the comparison indicates that the detected level of neural inspiratory activation of the patient is equal to the determined target level.

29. A system for delivering combined positive and negative pressure assist ventilation as defined in claim 23, wherein the controller controls the negative pressure ventilator to apply a constant negative pressure around the patient's ribcage and/or abdomen during patient's inspiration.

30. A system for delivering combined positive and negative pressure assist ventilation as defined in claim 23, wherein the controller is responsive to the neural inspiratory activation to control the negative pressure ventilator.

31. A system for delivering combined positive and negative pressure assist ventilation as defined in claim 23, comprising:
means for determining a target level of an abdominal pressure swing of the patient; and
a sensor of a level of abdominal pressure swing of the patient;
the controller comprising a comparator of the sensed level of abdominal pressure swing with the determined target level to control the negative pressure ventilator as a function of the comparison.

32. A system for delivering combined positive and negative pressure assist ventilation as defined in claim 31, wherein the controller increases a level of negative pressure applied around the patient's ribcage and/or abdomen when the comparison indicates that the sensed level of abdominal pressure swing of the patient is higher than the determined target level.

33. A system for delivering combined positive and negative pressure assist ventilation as defined in claim 31, wherein the controller decreases a level of negative pressure applied around the patient's ribcage and/or abdomen when the comparison indicates that the sensed level of abdominal pressure swing of the patient is lower than the determined target level.

34. A system for delivering combined positive and negative pressure assist ventilation as defined in claim 31, wherein the controller maintains a present level of negative pressure applied around the patient's ribcage and/or abdomen when the comparison indicates that the sensed level of abdominal pressure swing of the patient is equal to the determined target level.

35. A system for delivering combined positive and negative pressure assist ventilation as defined in claim 23, comprising:
means for adjusting levels of the positive and negative pressures to avoid application of excessive positive pressure to the patient's airways and thereby minimize hemodynamic adverse effects.

36. A system for delivering combined positive and negative pressure assist ventilation as defined in claim 23, wherein the controller controls application of the positive pressure to the patient's airways as a function of the detected neural inspiratory activation.

37. A system for delivering combined positive and negative pressure assist ventilation as defined in claim 36, wherein the controller synchronizes triggering and termination of the application of the positive pressure to the patient's airways as a function of the detected neural inspiratory activation.

38. A system for delivering combined positive and negative pressure assist ventilation as defined in claim 23, wherein the controller synchronizes triggering and termination of the application of negative pressure with triggering and termination of the application of positive pressure.

39. A system for delivering combined positive and negative pressure assist ventilation as defined in claim 23, wherein the controller controls a level of the negative pressure applied around the patient's ribcage and/or abdomen as a function of the detected neural inspiratory activation.

40. A system for delivering combined positive and negative pressure assist ventilation as defined in claim 23, further comprising means for applying a constant Negative End-Expiratory Pressure over the abdomen to adjust an end-expiratory lung-volume.

41. A system for delivering combined positive and negative pressure assist ventilation as defined in claim 40, wherein the constant Negative End-Expiratory Pressure applying means comprises means for applying the constant Negative End-Expiratory Pressure over the abdomen in combination with inspiratory negative pressure assist ventilation.

42. A system for delivering combined positive and negative pressure assist ventilation as defined in claim 40, wherein the constant Negative End-Expiratory Pressure applying means comprises means for applying the constant Negative End-Expiratory Pressure over the abdomen in proportional response to tonic inspiratory muscle activation occurring during expiration.

43. A system for delivering combined positive and negative pressure assist ventilation as defined in claim 23, comprising:
a pressure sensor for measuring an abdominal pressure of the patient;
wherein the controller further controls the negative pressure in response to a measured abdominal pressure of the patient.

44. A system for delivering combined positive and negative pressure assist ventilation to a patient, comprising:
means for detecting neural inspiratory activation of the patient;
first means for applying a positive pressure to the patient's airways to inflate the patient's lungs;
second means for applying a negative pressure around the patient's ribcage and/or abdomen in order to reduce a load imposed by the ribcage and/or abdomen on the patient's lungs; and means connected to the first and second pressure applying means for controlling application of the positive and negative pressures in response to the detected neural inspiratory activation;

wherein the means for controlling are responsive to the detected neural inspiratory activation to control a level of positive pressure applied by the positive pressure ventilator.

45. A system for delivering combined positive and negative pressure assist ventilation as defined in claim 44, wherein the means for applying a negative pressure comprises means for obtaining an intrathoracic pressure estimate by measuring an airway pressure deflection during a patient's airway occlusion.

46. A system for delivering combined positive and negative pressure assist ventilation as defined in claim 45, wherein, in case of intrinsic PEEP, the intrathoracic pressure estimate obtaining means comprises means for conducting an extrapolation of the intrathoracic pressure estimate for the period between an onset of electrical activity of the patient's diaphragm activity and an onset of the patient's airway pressure deflection.

47. A system for delivering combined positive and negative pressure assist ventilation as defined in claim 44, comprising:

means for measuring an abdominal pressure of the patient; and means for further controlling application of the negative pressure in response to the measured abdominal pressure.

* * * * *

UNITED STATES PATENT AND TRADEMARK OFFICE
CERTIFICATE OF CORRECTION

| | | |
|---|---|---|
| PATENT NO. | : 7,909,034 B2 | Page 1 of 1 |
| APPLICATION NO. | : 10/576636 | |
| DATED | : March 22, 2011 | |
| INVENTOR(S) | : Sinderby et al. | |

It is certified that error appears in the above-identified patent and that said Letters Patent is hereby corrected as shown below:

In claim 16, column 12, line 11, delete "rib age".

In claim 46, column 16, line 5, delete "activity".

Signed and Sealed this
Fourteenth Day of June, 2011

David J. Kappos
*Director of the United States Patent and Trademark Office*